United States Patent [19]

Goald

[11] 4,369,788
[45] Jan. 25, 1983

[54] REVERSED FORCEPS FOR MICRODISC SURGERY

[76] Inventor: Harold J. Goald, 4600 King St., Suite 5L, Alexandria, Va. 22302

[21] Appl. No.: 279,836

[22] Filed: Jul. 2, 1981

Related U.S. Application Data

[63] Continuation of Ser. No. 117,203, Jan. 31, 1980, abandoned.

[51] Int. Cl.$^3$ .............................................. A61B 17/28
[52] U.S. Cl. .................................... 128/321; 128/305; 128/751
[58] Field of Search ............... 128/321, 326, 305, 325, 128/751, 312, 318, 322; 227/DIG. 1 B; 81/355; 433/153

[56] References Cited

U.S. PATENT DOCUMENTS

| | | | |
|---|---|---|---|
| 2,668,537 | 2/1954 | Kapp | 128/318 |
| 2,790,437 | 4/1957 | Moore | 128/321 X |
| 3,585,985 | 6/1971 | Gould | 128/318 X |
| 3,814,102 | 6/1974 | Thal | 128/325 X |
| 4,043,343 | 8/1977 | Williams | 128/321 |

FOREIGN PATENT DOCUMENTS 110789 5/1964 Czechoslovakia ................. 128/312

OTHER PUBLICATIONS

"Microlumbar Discectomy", by Goald, *Virginia Medical*, Aug. 1976.
"Microsurgical Removal of Lumbar Herniated Nucleus Pulposus", by Goald, F.A.C.S, Surg. Gynec. & Obstec., Aug. 1979, vol. 149, pp. 247–248.

*Primary Examiner*—Michael H. Thaler
*Attorney, Agent, or Firm*—Fidelman, Wolffe & Waldron

[57] ABSTRACT

Forceps of the alligator jaw type, that can be held by a surgeon in a reversed backhand grip while observing the movable jaw during microlumbar discectomy, comprise three linkage devices for resisting twisting forces that tend to separate the sliding arms during removal of gristle. These devices are a slide slot within the rigid arm member in combination with a butt portion of the slideable arm member, a pivot slot within the slideable arm member in combination with a lug portion of the pivotable handle member, and a pin portion of the locking pin member in combination with aligned holes in the slideable arm member and pivotable arm member. The third device simultaneously keeps the forceps in assembled relationship; yet its removal instantly permits disassembly thereof. These three devices are combined within a very compact part of the instrument.

Usage of the forceps in a reversed backhand grip enables a surgeon to rest the heel of his hand upon the patient's back and exert a very light touch within the two-millimeter opening so that a plunge beyond the anterior side of the disc can be obviated, the arms can be inserted at a flatter angle beneath the nerves for pulling out gristle, and the operating time can be reduced to about 30 minutes.

7 Claims, 7 Drawing Figures

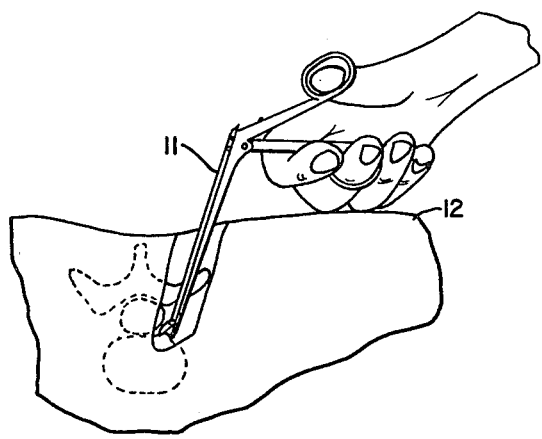
Fig.1
PRIOR ART
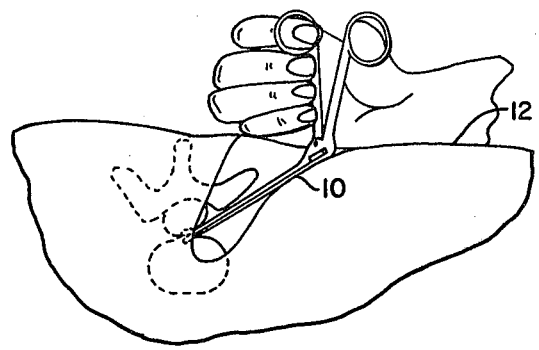
Fig.2
Fig.3
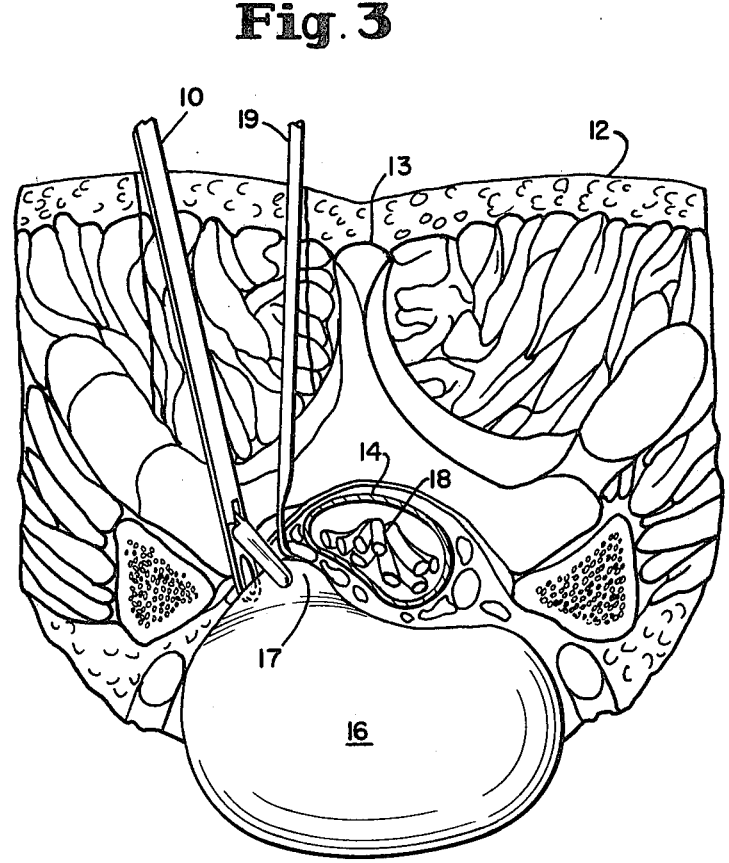

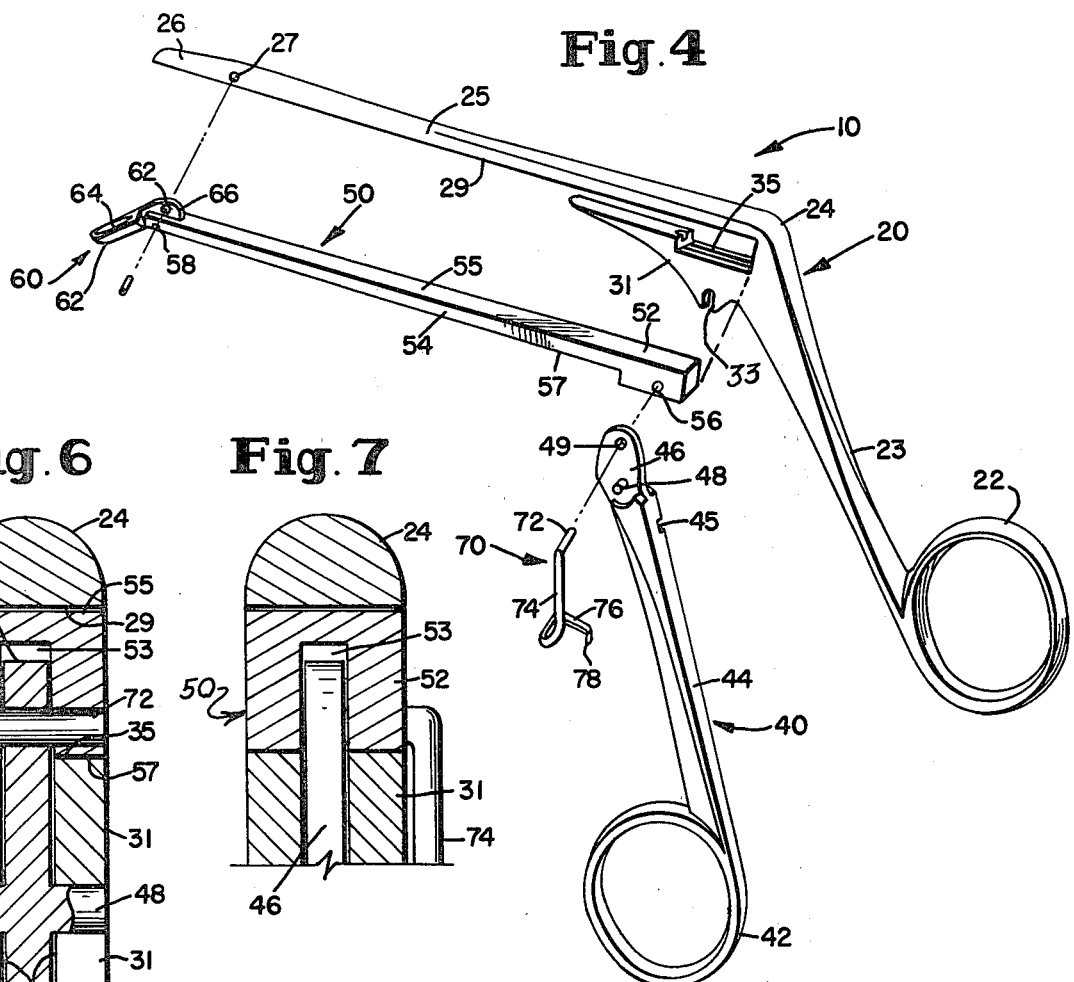
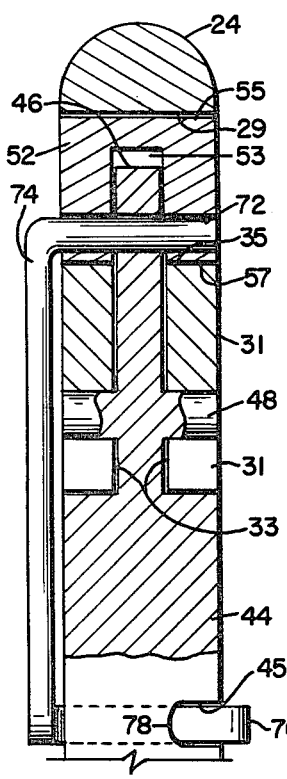
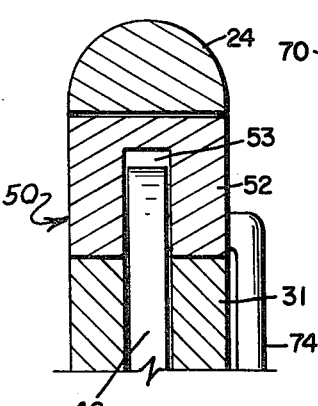
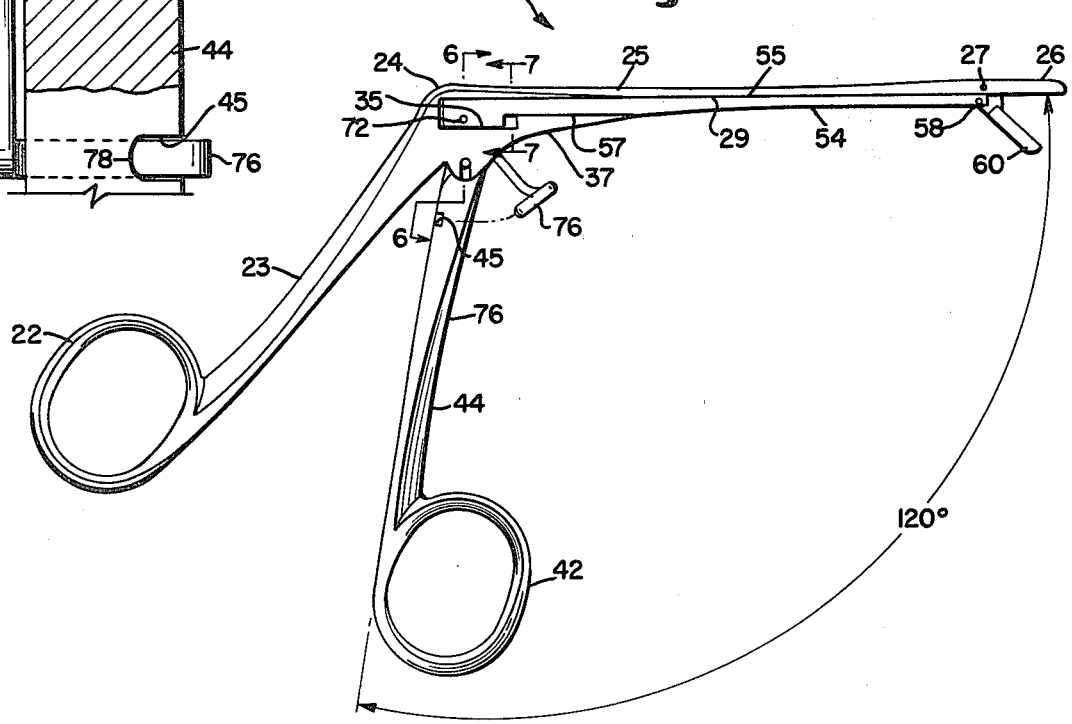

REVERSED FORCEPS FOR MICRODISC SURGERY

This is a continuation of application Ser. No. 117,203, filed Jan. 31, 1980, now abandoned.

BACKGROUND OF THE INVENTION

1. Field of the Invention

This invention relates to devices provided with pivotable members connected to jaws for grasping parts of a body or articles within a body. It particularly relates to forceps for use in microsurgery and especially relates to forceps for use in microlumbar discectomy.

2. Review of the Prior Art

In the center of an intervertebral disc in the human body, there is an elastic semi-fluid mass, termed the nucleus pulposus, which may rupture or prolapse entirely or in part into the spinal canal, frequently causing chronic sciatica. Disc surgery to correct this situation has been carried out since 1934 in what has become a standard operation, termed a lumbar laminectomy. It requires a four-inch incision in the patient's back and attempted removal by the surgeon of all the disc material in the intervertebral space.

As a surgeon comes closer to the front of the disc, there is always a risk of a "plunge" through its anterior disc surface that can injure the abdominal structures, including the great vessels and the intestines. Indeed, 100–200 deaths from such plunges have been reported in the medical literature since 1934. It is believed that a plunge can be difficult to avoid because the forceps are held in the surgeon's hand in the forehand grip that enables movements of the forceps to be controlled through his shoulder, elbow, wrist, and fingers. But as the front of the disc is reached, it becomes very difficult for the surgeon to retain the extremely precise control that is needed to avoid a plunge in the tense and tiring conditions of a standard lumbar laminectomy, which requires about 80 minutes.

A microlumbar discectomy operation was devised by Dr. Robert W. Williams of Las Vegas, Nev., in 1972. He reported his results to the American Association of Neurological Surgeons in April 1975. These techniques are described in "Surgical Techniques, Micro-Lumbar Discectomy", by R. W. Williams, Codman and Shurtleff, Inc., Randolph, Mass., 1977.

Dr. Williams invented a microdisc forceps (described in U.S. Pat. No. 4,043,343) which comprises a pair of handles connected to rings, a pair of slidingly parallel extension arms of which the fixed arm is rigidly connected to the rearward handle and terminates in a fixed jaw, a pivotable jaw connected to the sliding arm, and a side-mounted locking member. The sliding arm is pivotally connected to the forward handle. Squeezing the handles toward each other causes the sliding arm to move forward and closes the jaws. The obtuse angle between the extension arms and the closed handles is about 120°. The pivotable jaw on the slideable extension arm is outside this obtuse angle. The surgeon sights along the extension arms while watching the movements of the pivotable jaw during microdisc surgery and while holding the instrument in a forehand grip.

The microlumbar discectomy operation is performed by the surgeon who uses the surgical microscope, with a nurse's assistance, without performing a laminectomy or curettement of the disc space. No assistant surgeon is needed.

As reported by Harold Gaold, M.D., in "Microlumbar Discectomy", *Virginia Medical,* August 1976, and in "Microsurgical Removal of Lumbar Herniated Nucleus Pulposus", *Surgery, Gynecology & Obstetrics,* August 1979, vol. 149, pages 247, 248, a one-inch skin incision is precisely centered by palpation from the lumbosacral notch over the interspace to be explored. The width of the incision is expanded by using an improved surgical retractor, invented by Dr. Williams and described in U.S. Pat. No. 4,034,746. The surgeon looks through a Zeiss OPM Number 1 operating microscope, having a 350 millimeter lens with a 20× eyepiece to furnish 25× magnification, while using a microscope lamp assembly invented by Dr. Williams to furnish high intensity illumination (U.S. Pat. No. 4,039,817). The ligamentum flavum is removed with a one-millimeter Kerrison punch, without doing a laminectomy. The nerve root is identified and is gently dissected off the underlying herniated nucleus pulposus. Then the nerve root is secured out of the field of the microscope without undue tension by a suction retractor invented by Dr. Williams (U.S. Pat. No. 4,049,000). The fibers of the annulus are penetrated bluntly by a dissector in order to part them, and a 90° nerve hook is used to loosen the herniated portion of the nucleus pulposus which is removed with a microdisc forceps having a jaw width of two millimeters. The surgeon generally steadies his operating hand, during the removal procedure, by resting the tip of this little finger against the patient's back as he slides the closed jaws of his forceps toward and into the herniated mass, up to the hinge which he can watch as he opens and closes the jaws of the forceps. He twists and pulls as much as necessary to remove gristle. He then withdraws the forceps completely from the incision, so that the nurse can remove the grasped material, and repeats the procedure.

Before removal of the herniated material, the epidural veins are easily seen and peeled off the surface of the disc, maintaining blood loss at about 30 milliliters. The fascia and the subcutaneous tissue are closed in layers. By parting the fibers of the annulus instead of cutting them, the retaining wall effect of the annulus is preserved. After the herniated portion has been removed, the sublayers of the annulus can be seen to close over the opening. The extradural fat surrounding the nerve root is preserved, thus minimizing the chance of adhesions postoperatively.

The entire operation for removal of a herniated nucleus pulposus according to the procedure developed by Dr. Williams requires about 45 minutes. In a follow-up study of 200 patients operated on over a 2¾ year period, the cure rate was 96%.

However, because the disc forceps are used in the forehand grip, there has always been a risk of a plunge. This risk may occur because the herniated nucleus pulposus is not homogenous. Thus the jaws may slide rapidly through necrotic tissue or slip into a cavity. In addition, the surgeon may observe sudden hemorrhaging and forget to stabilize his hand with his little finger so that he is controlling the forceps with his entire arm while under unexpected pressure.

Moreover, a disc may herniate toward the center when it ruptures. The surgeon may therefore need to get toward the center of the disc and thus be under many nerves while manipulating his forceps over the edge of the steel retractor that is expanding the incision. In doing so, the surgeon moves his hand downwardly in order to manipulate the alligator jaws and the extension arms of the disc forceps in as horizontal a movement as possible in the forehand grip, with the ring finger through the forward ring and the thumb through the rearward ring. But in doing so his hand and the rear ring of the forceps hit the back of the patient, so that he is unable to place the slideable arms of the instrument at as flat an angle with respect to the patient's back as he requires, in order to be able to slide the jaws and extension arms farther under the surface of the annulus for pulling out gristle that is beneath the nerve roots.

If a surgeon encounters this situation while performing a microlumbar discectomy, he could reverse his forceps and attempt to use them with a backhand grip. However, the movable jaw is then beneath the fixed jaw and must open downwardly toward the fibrocartilaginous disc after insertion of the closed jaws into the herniation. In this position it is difficult to see what the moveable jaw is doing since the movable part is underneath and less visible. This is particularly important since the moveable jaw may break and disappear into the disc space.

There is consequently a need for a reversed microdisc forceps having its movable jaw within the obtuse angle formed by the slideable arms and the handles, whereby the movable jaw is uppermost while the forceps are held in a backhand grip.

SUMMARY OF THE INVENTION

It is accordingly an object of this invention to provide reversed microdisc forceps that are held in a backhand grip, whereby a surgeon can rest his forehand on the patient's back during microlumbar discectomy.

It is also an object to provide reversed microdisc forceps having its pivotable jaw within the obtuse angle between the extension arms and the handles.

It is further an object to provide reversed microdisc forceps having anti-twist means furnishing additional support for the slideable arm during sliding movements thereof and during twisting usage of the instrument, whereby disengagement of the arms is minimized without need for a side-mounted locking member.

It is another object to provide reversed microdisc forceps having a connecting means for the slideable arm and the pivotable handle that provides further support during twisting usage of the instrument but permits quick disassembly thereof without being attached to the stationary handle.

In accordance with these objects and the principles of this invention, reversed microdisc alligator forceps are herein described that comprise a rigid member, a pivotable handle member, a slideable arm member, a pivotable jaw member, and a locking pin member.

The rigid member comprises a handle, having a thumb ring at one end thereof and a shoulder at the other end thereof, and an arm or shank that is rigidly connected to the shoulder and disposed at about an angle of 130° to the handle. This fixed arm has a rigid jaw and a jaw hole at its forward end and a major slide surface along one side. It also comprises a pivot portion that is connected to the handle and disposed opposite the shoulder across a longitudinally disposed support slot. The pivot portion comprises a pivot notch and a pair of minor slide surfaces alongside the support slot.

The pivotable handle member comprises a handle having a finger ring at one end thereof and a lug portion at the other end thereof. The lug portion comprises a pivot pin and a connecting hole. The handle also has a clasp recess along one edge.

The slideable arm member comprises a butt portion, a longitudinally disposed pivot slot that is aligned transversely to the support slot, an arm or shank portion, a major slide surface, a minor slide surface, a connecting hole, and a jaw hole.

The pivotable jaw member comprises a rigidly attached lug which is provided with a pair of cutting edges, a jaw recess, and a hole. The locking pin member comprises a pin portion, a shank portion, a bight portion, and a clasp portion. A first jaw pin fits within aligned holes in the pivotable jaw member and the slideable arm member. A second jaw pin fits within the jaw hole of the rigidly connected arm.

The lug portion of the pivotable handle member fits pivotally within the pivot slot of the slideable arm member, so that their connecting holes coincide and are maintained in alignment by the pin portion of the locking pin member. The clasp portion of the locking pin member fits over the pivotable handle member and engages the clasp recess.

The reversed microdisc forceps are used in a reversed backhand grip by a right- or left-handed surgeon with his thumb within the thumb ring and his forefinger within the finger ring while his remaining three fingers are held at a distance from both handles. This reversed backhand grip on the microdisc forceps during microlumbar discectomy operations permits resting of the surgeon's hand on the patient's back or on a stack of towels, manipulation of the handles by movements of the forefinger, thumb and wrist only, slideable insertion of forceps as a probe, accurate and non-tiring control of the instrument to obviate a plunge, observation of the pivotable jaw by the surgeon, usage of the instrument at a flat angle approaching horizontal, and a fast operating time for removing a herniated lumbar nucleus pulposus. While resting the heel of his hand on the patient's back and observing the incision through the binocular surgical microscope, he moves the jaws of the forceps into the incision with its arms at a selected degree of flatness with respect to a patient's back. By moving his forefinger forwardly, the surgeon raises the pivotable jaw so that he can see precisely which portion of the herniated pulposus that he wishes initially to grasp. During successive insertion of the instrument into the herniated mass, he buries the jaws only as far as the jaw hinge, as further insurance against a plunge, and observes the hinge as he opens and closes the moveable jaw, away from the underlying disc.

BRIEF DESCRIPTION OF THE DRAWINGS

The invention may be more fully understood by reference to the drawings which illustrate the prior art and the subject matter of the invention as a whole.

FIG. 1 is a transverse section through a patient's body which shows one of the lumbar vertebrae and a disc which has herniated so that its bulging nucleus pulposus is pressing against the nerves thereabove, the sides of the incision being held apart by a steel retractor while the reversed microdisc forceps of this invention are contacting the herniated nucleus pulposus for removal thereof.

FIG. 2 is a diagrammatic cross-section, similar to FIG. 1 in which disc forceps of the prior art, such as the Williams forceps, are being used in a microlumbar discectomy.

FIG. 3 is a similar diagrammatic section of a patient's body in which the reversed microdisc forceps of the invention are being used in the same microlumbar discectomy.

FIG. 4 is an exploded view of the components of the reversed microdisc forceps of the invention.

FIG. 5 is a side view of the assembled microdisc forceps, showing the other side of that shown in FIG. 4.

FIG. 6 is a section through the shoulder area of the reversed microdisc forceps of FIGS. 4 and 5, taken in the direction of the arrows 6—6 in FIG. 5.

FIG. 7 is a similar section, taken closer to the jaws but looking the other way in the direction of the arrows 7—7 in FIG. 5.

DESCRIPTION OF THE PREFERRED EMBODIMENTS

Viewing the instrument as shown in side view in FIG. 5, the lower arm is the moveable arm, unlike such instruments as the Gould forceps (U.S. Pat. No. 3,585,985), the Thal forceps (U.S. Pat. No. 3,814,102), and the Williams forceps (U.S. Pat. No. 4,043,343). The lower arm in FIG. 5 may be termed the inside arm, because it is inside the obtuse angle formed between the arms and the handles, but it is not the lower arm when used in its operating position. The jaw at the end of the inside arm is the moveable jaw, again unlike the Gould, Thal, and Williams forceps. The reason therefor is that the moveable jaw is the one that must be kept in view by the surgeon while he is operating to remove the herniated nucleus pulposus. Furthermore, it must not open, by moving downwardly to catch upon tissue while the instrument is being slid, as a probe, over the side of the incision.

The reversed microdisc forceps, as shown in FIGS. 4 and 5, comprise a rigid member 20, a pivotable handle member 40, a slideable arm member 50, a pivotable jaw member 60, and a locking pin member 70. Pivotable handle member 40 is attached pivotally to rigid member 20 by a pivot pin 48 and is attached to slideable arm member 50 by locking pin member 70, in addition to pivotal fit within a pivot slot at the rear end of arm member 50.

Rigid member 20 comprises a thumb ring 22, a handle 23 attached to the thumb ring, an arm or shank 25, a shoulder 24 rigidly connecting arm 25 and handle 23, a pivot portion 31, and a rigid jaw 26 as the terminus of arm 25. A jaw hole 27, as is known in the art, is available for receiving a jaw pin 28. Major slide surface 29 is along one side of arm 25. Opposite shoulder 24 and forming a slot with surface 29 are two minor slide surfaces 35 in pivot portion 31 which also includes a pivot notch 33.

Pivotable handle member 40 comprises a finger ring 42, a handle 44 which is attached to finger ring 42, a clasp recess 45 along one side of handle 44, a relatively thin lug portion 46, a pivot pin 48 which is transversely disposed to lug portion 46 and on each side thereof, and a connecting hole 49.

Slideable arm member 50 comprises a butt portion 52, a pivotal slot 53 at its rear end, an arm or shank portion 54, a major slide surface 55 which engages slide surface 29, a connecting hole 56 for attachment to member 40, a pair of slide surfaces 57 for dual engagement with slide surfaces 35, a jaw hole 58, and an arm pin which fits into jaw hole 58.

Pivotable jaw member 60 comprises a jaw 62, a lug 64, a hole 66 in lug 64 which is engaged by jaw pin 28 within jaw hole 27, cutting edges 68, and a jaw recess 65.

Locking pin member 70 comprises a pin portion 72 which enters connecting holes 49 and 56, a shank portion 74 which overlies both pivot portion 31 and a part of handle member 40, a bight portion 76 which wraps partially around handle 24, and a clasp portion 78 which snaps into place in clasp recess 45.

A surgeon uses the reversed microdisc forceps of FIGS. 4 and 5 by placing his thumb, if he is right handed, through thumb ring 22 and his forefinger through finger ring 42, while his other fingers are spaced from handle 44. He maintains both thumb and forefinger at an angle to rings 22,42 and braces them against opposite sides of these rings so that he can accurately control all movements of jaws 26,62. He additionally rests the ulnar side or heel of his hand against the patient's back or upon a stack of towels while holding the forceps in this reversed backhand grip. As he moves his forefinger toward his thumb, the superior jaw or cup 62 bites down on inferior jaw or cup 26.

When a disc 16 has ruptured in the middle, as seen clearly in FIG. 3, forcing its nucleus pulposus 17 toward the middle and directly into the spinal canal 14 and against nerves 18, disc forceps 11 of the prior art, such as the Gould, Thal, and Williams forceps, which are held in a forehand grip, can not be moved downwardly toward the patient's back 12 sufficiently to reach under nerves 18 into a herniated nucleus pulposus 17, as seen in FIG. 1. It is not possible to maintain the same biting mobility of the top cup when the surgeon reverses the instrument unless the linkage is also reversed as shown in FIG. 2.

When a surgeon inserts forceps 10 into a herniation and grasps gristle, he frequently twists the instrument clockwise or counterclockwise with considerable force. A counterclockwise movement of forceps 10 illustrated in FIG. 7 causes butt portion of slidable arm member 50 to tend to rotate. The slide slot, disposed longitudinally in rigid member 20, has sufficient width along its slide surfaces 29,35 that a first twist-resisting couple is formed within it, exerting pressure upon slide surfaces 55,57 of slideable arm member 50. Simultaneously, a second twist-resisting couple is formed within lug portion 46 of pivotable handle member 40 and exerts pressure upon surfaces of pivotal slot 53. Also substantially simultaneously, unless the holes have become worn, a third twist-resisting couple forms within lug portion 46 and exerts pressure upon pin portion 72 within hole 49.

Usage of forceps 10 in a reversed backhand grip for performing numerous microlumbar discectomies has established an operating time of about 19 minutes as compared to about 37 minutes while using the Williams forceps in a forehand grip for the same minimal conservative operation which permits the patient to return to his home in less than three days.

The reversed microdisc forceps 10 are additionally useful in various operations requiring precise manipulations and extraction of material within confined spaces, such as in brain and joint microsurgery and in removal of tumors from many parts of the body. Extracting tumors from the brain, for example, can require a four-hour operation and is very tiring for a surgeon, so that having forceps that are adapted for reversed backhand grasping can be quite helpful. In general, any operation involving the extraction of pathologic material from complex structures within the human body can be aided by the presence of reversed forceps 10.

Arms 25,54 can be of any desired length and are preferably provided with a longitudinally disposed lug along one major slide surface 29,57 that slides within a narrow slot within the opposite slide surfaces 57,29 in order to inhibit dislocations of arms 25,54 when the instrument 10 is twisted. A suitable length for arms 25,54 is 5.5 mm for microdisc surgery.

Jaws 26,62 are preferably 8-10 mm in length from hinge to tip and 1-2 mm in width. Narrow jaws are particularly desirable for operations on people having degenerated discs. The jaws can also be provided with a tooth and matching recess at their tips.

Because it will be readily apparent to those skilled in the art that innumerable variations, modifications, applications, and extensions of the examples and principles hereinbefore set forth can be made without departing from the spirit and scope of the invention, what is herein defined as such scope and is desired to be protected should be measured, and the invention should be limited, only by the following claims.

What is claimed is:

1. A reversed grip microdisc forceps comprising:
   a rigid member formed overall in the general shape of an obtuse angle with a shoulder portion at the angle, a handle and finger grip portion as one leg of the angle, hereinafter termed the rear leg and an arm portion as the forward leg of the angle said arm portion having a slide surface thereon on the side face thereof included within the obtuse angle and a fixed jaw at the forward end of said arm portion;
   a handle and finger grip member positioned within the obtuse angle pivotally secured to the shoulder portion of said rigid member opposing the handle and finger grip rear leg;
   a slidable arm positioned within the obtuse angle locked at the butt end thereof to said handle and finger grip member adjacent said aforementioned arm portion in an upper fixed arm, lower slidable arm relationship whereby pivoting said handle and finger grip member toward the handle and finger grip portion of said rigid member causes the slidable arm to move, said slidable arm having a first slide surface thereon along the top thereof matched to the aforementioned slide surface on the arm portion of said rigid member, said slidable arm having at least one second slide surface on the bottom thereof at the butt end thereof matched to the hereinafter defined slide surface on the shoulder portion of said rigid member;
   said shoulder portion being bifurcated into upper and lower legs with the upper leg thereon being the arm portion of said rigid member, the lower leg thereon having thereon a slide surface matched to the said second slide surface on said slidable arm, the upper and lower legs on said shoulder portion providing therebetween above and below a slide slot into which the butt end of the slidable arm fits and wherein the slidable arm slides; and,
   a pivotable jaw member hingedly attached to said slidable arm at the front end thereof opposite the fixed jaw within the obtuse angle therefrom, opening and closing to said fixed jaw as said slidable arm is caused to slide by pivoting movement of said handle and grip member.

2. The forceps of claim 1 wherein said second slide surface on said slidable arm and the slide surface on said lower leg of the bifurcated shoulder portion are stepped surfaces.

3. The forceps of claim 1 wherein:
   (a) the butt portion of said slidable arm contains a pivot slot which is intersected by a pin opening;
   (b) said handle member contains a lug which fits pivotally within said pivot slot and is intersected by a pin opening; and,
   (c) a locking pin member which fits within both said pin openings thereby locking together said slidable arm and said handle and finger grip member.

4. The microdisc forceps of claim 3 wherein said locking pin member locking said slidable arm to said handle and finger grip member is removable.

5. A forceps of the alligator jaw type having an improved anti-twist construction comprising:
   a rigid member formed overall in the general shape of an obtuse angle with a shoulder portion at the angle, a handle and finger grip portion as one leg of the angle, hereinafter termed the rear leg, and an arm portion as the forward leg of the angle said arm portion having a slide surface thereon and a fixed jaw at the forward end of said arm portion;
   a handle and finger grip member positioned within the obtuse angle pivotally secured as hereinafter defined to the shoulder portion of said rigid member opposing the handle and finger grip rear leg;
   a slidable arm positioned within the obtuse angle locked at the butt end thereof to said handle and grip member adjacent said aforementioned arm portion in an upper fixed arm, lower slidable arm relationship whereby pivoting said handle and finger grip member toward the handle and finger grip portion of said rigid member causes the slidable arm to move, said slidable arm having a first slide surface thereon along the top thereof matched and positioned relative to the aforementioned slide surface on the arm portion of said rigid member to slide thereon, said slidable arm having at least one second slide surface on the bottom thereof at the butt end thereof matched and positioned relative to the hereinafter defined slide surface on the shoulder portion of said rigid member to slide thereon;
   said shoulder portion being bifurcated into upper and lower legs, the upper leg thereon being the arm portion of said rigid member, the lower leg having thereon a slide surface matched and located relative to said second slide surface on said slidable arm for sliding purposes, the upper and lower legs providing therebetween above and below a slide slot into which the butt end of said slidable arm fits and wherein said slidable arm slides;
   a lug on said handle and finger grip member, and a pivot slot in said shoulder portion and in the butt end of said slidable arm wherein said lug is disposed, a pin opening through said shoulder portion intersecting said lug and pivot slot of said butt end, and a locking pin positioned in said pin opening thereby pivotally securing said handle and finger grip member to said shoulder portion and locking said handle and finger grip member to said slidable arm; and
   a pivotable jaw member hingedly attached to said slidable arm at the front end thereof opposite the fixed jaw, opening and closing to said fixed jaw appropriately when said slidable arm is caused to slide by pivoting movement of said handle and grip member.

6. The forceps of claim 5 wherein said locking pin is removable for ready disassembly of the forceps.

7. The forceps of claim 5 wherein the slide surface on said other leg of the bifurcated shoulder portion is stepped and the second slide surface on said slidable arm is correspondingly stepped.

* * * * *